(12) United States Patent
Kappel et al.

(10) Patent No.: US 12,089,826 B2
(45) Date of Patent: Sep. 17, 2024

(54) ARTICULATION JOINT WITH BENDING MEMBER

(71) Applicant: Boston Scientific Scimed, Inc., Maple Grove, MN (US)

(72) Inventors: Gary Kappel, Acton, MA (US); William Lucas Churchill, Bolton, MA (US); Francis MacNamara, Sunnyvale, CA (US); Eric Gutierrez, Bedford, TX (US); Larry Stanton, Burlington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1000 days.

(21) Appl. No.: 16/801,367

(22) Filed: Feb. 26, 2020

(65) Prior Publication Data

US 2020/0187926 A1 Jun. 18, 2020

Related U.S. Application Data

(63) Continuation of application No. 15/434,670, filed on Feb. 16, 2017, now Pat. No. 10,610,209, which is a
(Continued)

(51) Int. Cl.
*A61B 17/00* (2006.01)
*A61B 17/072* (2006.01)
(Continued)

(52) U.S. Cl.
CPC ...... *A61B 17/00234* (2013.01); *A61B 17/072* (2013.01); *A61B 17/29* (2013.01);
(Continued)

(58) Field of Classification Search
CPC . A61B 17/00; A61B 17/00234; A61B 17/072; A61B 17/29; A61B 2017/00305;
(Continued)

(56) References Cited

U.S. PATENT DOCUMENTS 5,618,294 A 4/1997 Aust
6,077,287 A 6/2000 Taylor et al.
(Continued)

*Primary Examiner* — Ahmed M Farah
(74) *Attorney, Agent, or Firm* — Bookoff McAndrews, PLLC

(57) ABSTRACT

The present disclosure provides an articulation joint that can include a plurality of articulation links, wherein each articulation link can include an elongate body having a proximal end, a distal end, an outer surface, and a first lumen extending from the proximal end to the distal end. Each articulation link can further include a plurality of arms extending radially outward from the elongate body, wherein each arm includes an inner end attached to the outer surface of the elongate body and a second lumen extending from a proximal side of the arm to a distal side of the arm. The articulation joint can also include a bending member positioned within the first lumen of the elongate body and a control member positioned within a plurality of second lumens, wherein each of the plurality of second lumens includes a common longitudinal axis.

19 Claims, 8 Drawing Sheets

Related U.S. Application Data continuation of application No. 13/961,301, filed on Aug. 7, 2013, now Pat. No. 9,610,068.

(60) Provisional application No. 61/694,371, filed on Aug. 29, 2012.

(51) Int. Cl.
*A61B 17/29* (2006.01)
*A61M 25/01* (2006.01)
*F16C 11/04* (2006.01)
*A61B 1/005* (2006.01)

(52) U.S. Cl.
CPC ......... *A61M 25/0138* (2013.01); *F16C 11/04* (2013.01); *A61B 1/0055* (2013.01); *A61B 2017/00314* (2013.01); *A61B 2017/00327* (2013.01); *A61M 25/0147* (2013.01); *Y10T 403/32008* (2015.01)

(58) Field of Classification Search
CPC ........... A61B 2017/00314; A61B 2017/00318; A61B 2017/00327; A61M 25/0138; A61M 25/0147; Y10T 403/32008
USPC ........................................................ 606/1
See application file for complete search history.

(56) References Cited

U.S. PATENT DOCUMENTS

| | | | |
|---|---|---|---|
| 8,236,016 B2 | 8/2012 | To et al. | |
| 9,204,783 B2* | 12/2015 | Kappel | A61M 25/0009 |
| 9,610,068 B2* | 4/2017 | Kappel | F16C 11/04 |
| 10,610,209 B2* | 4/2020 | Kappel | A61B 17/072 |
| 2005/0131279 A1* | 6/2005 | Boulais | A61B 1/0016 |
| | | | 600/141 |
| 2007/0135803 A1* | 6/2007 | Belson | A61B 1/00154 |
| | | | 606/1 |
| 2008/0045986 A1 | 2/2008 | To et al. | |
| 2008/0286036 A1* | 11/2008 | Macnamara | A61B 1/0055 |
| | | | 29/896.9 |
| 2008/0300462 A1 | 12/2008 | Intoccia | |
| 2009/0259141 A1 | 10/2009 | Ewers et al. | |
| 2010/0076451 A1 | 3/2010 | Zwolinski et al. | |
| 2012/0197241 A1* | 8/2012 | Golden | A61B 1/008 |
| | | | 606/1 |
| 2013/0131695 A1 | 5/2013 | Scarfogliero et al. | |
| 2014/0066952 A1 | 3/2014 | Kappel et al. | |

* cited by examiner

ARTICULATION JOINT WITH BENDING MEMBER

CROSS-REFERENCE TO RELATED APPLICATIONS

This application is a continuation of U.S. patent application Ser. No. 15/434,670, filed on Feb. 16, 2017, which is a continuation of U.S. patent application Ser. No. 13/961,301, filed on Aug. 7, 2013, now U.S. Pat. No. 9,610,068, which claims the benefit of priority from U.S. Provisional Application No. 61/694,371, filed on Aug. 29, 2012, each of which is herein incorporated by reference in its entirety.

TECHNICAL FIELD

The following disclosure relates generally to medical devices and in particular to articulation joints for use with steerable medical devices.

BACKGROUND

As an alternative to performing more invasive surgical procedures, many physicians use minimally invasive medical devices to diagnose and treat patients. A minimally invasive medical device, such as an endoscope or a catheter, often has an elongate shaft that is inserted into the patient. The shaft can include one or more channels through which an instrument can be placed to access a site within the patient.

In order to guide the medical device to a desired location, the shaft can include one or more control members that may be controlled by an actuator located proximally along the device. By tensioning a control member, the shaft's distal tip can be bent in a desired direction. To facilitate this bending, the medical device can include an articulation joint located along the shaft or at the distal end of the device. The articulation joint is designed to permit bending of the shaft in a desired direction, whereby bending can be controlled by applying a force to one or more control members.

Most articulation joints found in steerable medical devices are made from stainless steel or other biocompatible materials. These devices can be expensive to manufacture and may have to withstand repeated sterilizations or cleanings. Despite these precautions, contaminants or disease may be passed from one patient to another. To reduce the risk of cross-patient contamination and to lower the cost of minimally invasive procedures, more affordable medical devices require development.

The present disclosure relates to improvements in an articulation joint for steerable medical devices that addresses at least some of the limitations of the prior art.

SUMMARY

According to one aspect of the present disclosure, an articulation joint can include a plurality of articulation links, wherein each articulation link can include an elongate body having a proximal end, a distal end, an outer surface, and a first lumen extending from the proximal end to the distal end. Each articulation link can further include a plurality of arms extending radially outward from the elongate body, wherein at least one arm of the plurality of arms includes a first end coupled to the outer surface of the elongate body and a second lumen. The articulation joint can also include a control member positioned within the second lumen.

In addition, the articulation joint may include one of more of the following features: an articulation link of the plurality of articulation links may include a support member fixedly attached to a second end of the at least one arm, the second lumen may include a longitudinal axis that may be transverse to a longitudinal axis of the at least one arm, an articulation link of the plurality of articulation links may include a contact surface configured to engage an adjacent articulation link to permit relative movement between the articulation link and the adjacent articulation link, wherein the contact surface includes at least one of a camming surface, a pivoting surface, a concave surface, and a convex surface, at least one of the plurality of articulation links may have a central longitudinal axis of the first lumen located asymmetrically relative to a central longitudinal axis of the at least one of the plurality of articulation links, a bending member positioned within the first lumen of the elongate body, wherein the bending member may include at least one of an elastomeric rod and spring, the spring may include a lumen configured to receive a medical device, the arms may be distributed symmetrically about the outer surface of the elongate body and define a region configured to receive a medical device, the plurality of articulation links may be positioned apart along a longitudinal axis such that the proximal end of a first articulation link and the distal end of a second articulation link located adjacent to the first articulation link are separated by a length of a bending member, and each of the second lumens may include a common longitudinal axis.

According to another aspect of the present disclosure, an articulation link can include an elongate body having a proximal end, a distal end, an outer surface, and a first lumen extending from the proximal end to the distal end, wherein the first lumen is configured to receive a bending member. The articulation link can also include a plurality of arms extending outward from the outer surface of the elongate body, each arm including an outer end having a second lumen extending from a proximal side of the arm to a distal side of the arm, the second lumen being configured to receive a control member.

According to yet another aspect of the present disclosure, an articulating medical device can include a plurality of articulation links, wherein each articulation link includes an elongate body having a longitudinal axis and a first lumen. Each articulation link can also include a plurality of arms extending transverse to the longitudinal axis and outward from the elongate body, each arm including a second lumen. The articulating medical device can also include a control member positioned within a plurality of second lumens, and a cover located about the plurality of articulation links.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made to exemplary embodiments of the invention, examples of which are illustrated in the accompanying drawings. Wherever possible, the same reference numbers will be used throughout the drawings to refer to the same or like parts.

Figure 1:
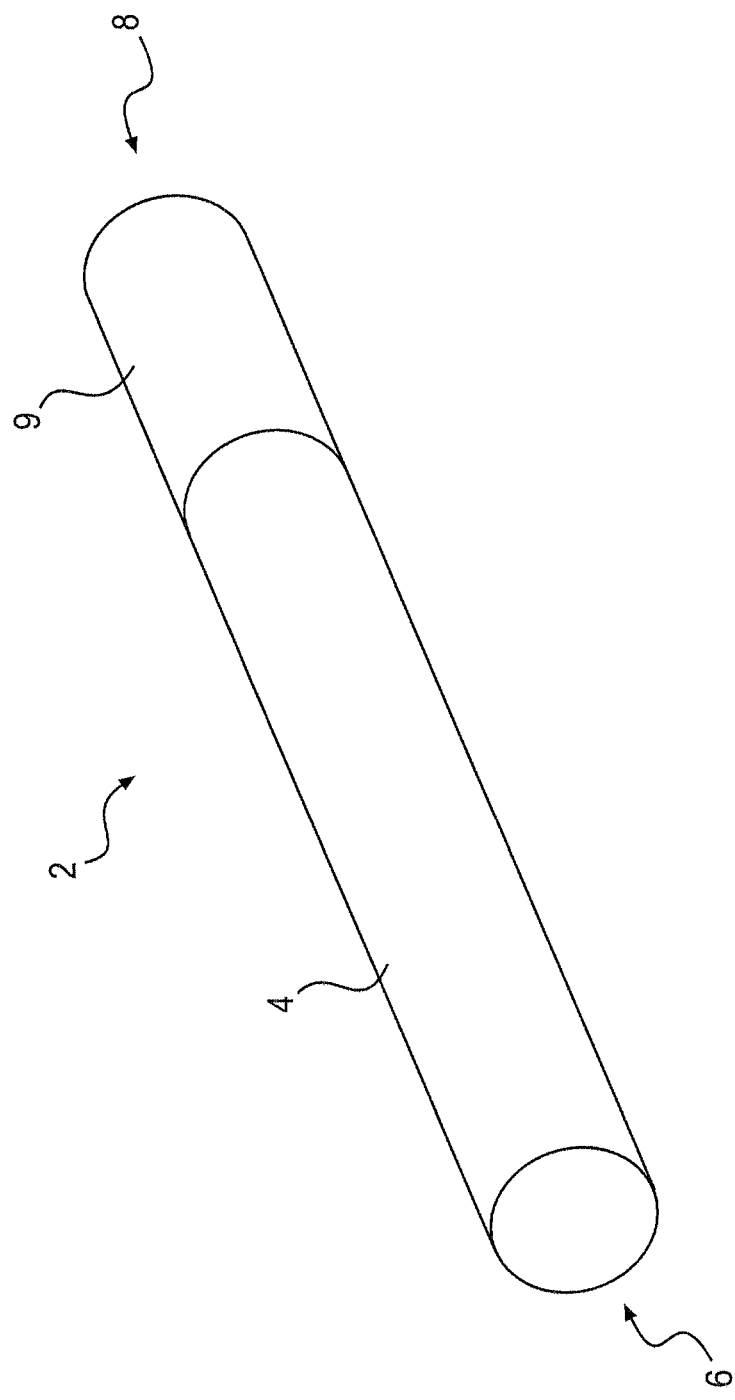
FIG. 1 is a perspective view of a device, according to an exemplary embodiment of the invention.

FIG. 1 depicts a device 2, according to an exemplary embodiment. Device 2 can include a medical device configured for use with a surgical method, including a therapeutic or diagnostic procedure. Device 2 can include an endoscope, a guide tube, a catheter, a guidewire, or other type of elongate medical device. In some embodiments, device 2 can include a flexible instrument, such as, for example, a grasper, a dissector, scissors, a stapler, an electrosurgical device, or other type of endoscopic or laparoscopic instrument. Further, device 2 may be used for procedures within or adjacent to various body organs, such as, an esophagus, a heart, a stomach, a pelvic area, a bladder, an intestine, or a gastrointestinal, urinary, or pulmonary tract.

Device 2 may be configured for insertion into a patient's body through an anatomical opening. In other embodiments, device 2 may be used in natural orifice transluminal endoscopic surgery (NOTES) procedures or single incision laparoscopic surgical (SILS) procedures. Accordingly, device 2 can be shaped and sized for placement into a patient via a body cavity or an incision.

Device 2 can be configured to operate with one or more instruments (not shown) used in various surgical procedures. For example, device 2 can include one or more lumens (not shown) configured to receive a grasper, a pair of scissors, a hook, an ablation device, or other type of surgical instrument. Device 2 may also be configured to operate with, or include, insufflation, irrigation, suction, imaging, or systems used in endoscopic, laparoscopic, or other surgical procedures.

Device 2 can include a shaft 4 having a proximal end 6 and a distal end 8. Proximal end 6 can be manipulated by an operator to control distal end 8. For example, proximal end 6 can include one or more knobs, dials, levers, triggers, handles, or other devices (not shown) configured to move distal end 8 relative to proximal end 6.

Shaft 4 can also include an articulating portion 9. As shown in FIG. 1, articulating portion 9 can be located at or near distal end 8. In other embodiments, articulating portion 9 can be located anywhere along shaft 4, or encompass the entire length of shaft 4. In operation, an operator can manipulate articulation portion 9 to move distal end 8 up, down, left, or right. As indicated above, the disclosed technology relates to improvements in an articulation joint for a steerable medical device.

According to some exemplary embodiments, articulation portion 9 can be configured to provide axial stiffness based on one or more structures located generally at or about a central region of articulation portion 9. For example, a central part of articulation portion 9 can be configured to provide most of the axial stiffness of articulation portion 9 while an outer part of articulation portion 9 may provide less axial stiffness than that provided by the central part of articulation portion 9. For example, as described below and shown in FIG. 7, a bending member 225 may be configured to provide more axial stiffness than the axial stiffness provided by a cover 220. An axially stiff center may not add significant bending stress to articulation portion 9, permitting lower bending stiffness.

As described below in more detail, a central part of articulation portion 9 may be configured to provide a major part of the load bearing for an articulation mechanism under tension. In addition to providing at least the majority of compressive load bearing, the central part may also provide a pivoting axis for articulation portion 9. Articulation portion 9 may also include an outer part that provides little or no compression strength. Accordingly, the outer part may be formed from low cost, low durometer plastic, or low durometer braid. Various embodiments of articulation portion 9 are described as follows.

Figure 2:
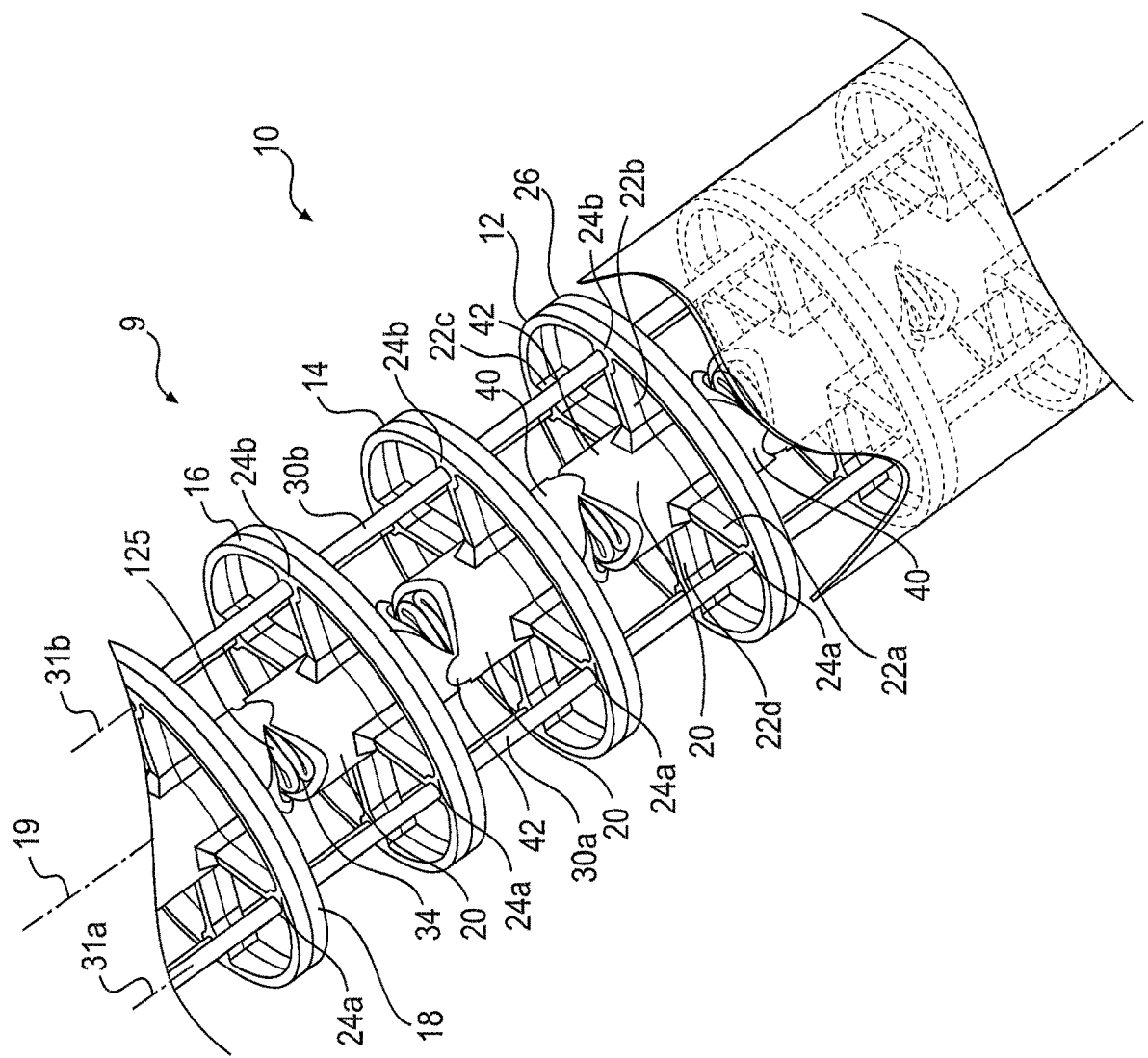
FIG. 2 illustrates an articulation joint, according to an exemplary embodiment of the invention.

FIG. 2 illustrates an articulation joint 10 in accordance with one embodiment of the disclosed technology. Articulation joint 10 can include a number of articulation links 12, 14, 16, 18. Each articulation link can include an elongate body 20 having a first lumen 23 (see FIG. 3) that can be configured to receive a bending member 125. Elongate body 20 can be cylindrical or another shape, and may include a longitudinal axis 19 extending along the length of elongate body 20.

Bending member 125 can be configured to flex to permit relative movement between articulation links 12-18. For example, bending member 125 can include a spring 34 (see FIG. 2), an elastomeric rod 127 (see FIG. 4), or another type of elastic member that may be located within first lumen 23. In some embodiments, spring 34 may be tightly wound or more loosely wound depending on the desired stiffness, looseness, or compressibility of articulation joint 10. To retain bending member 125 in articulation links 12-18, one or more elongate bodies 20 may be fixedly coupled to bending member 125. For example, a proximal-most or a distal-most elongate body 20 can be fixedly attached to bending member 125 by a friction fit, crimping, welding, adhesive, or another joining method.

Figure 3:
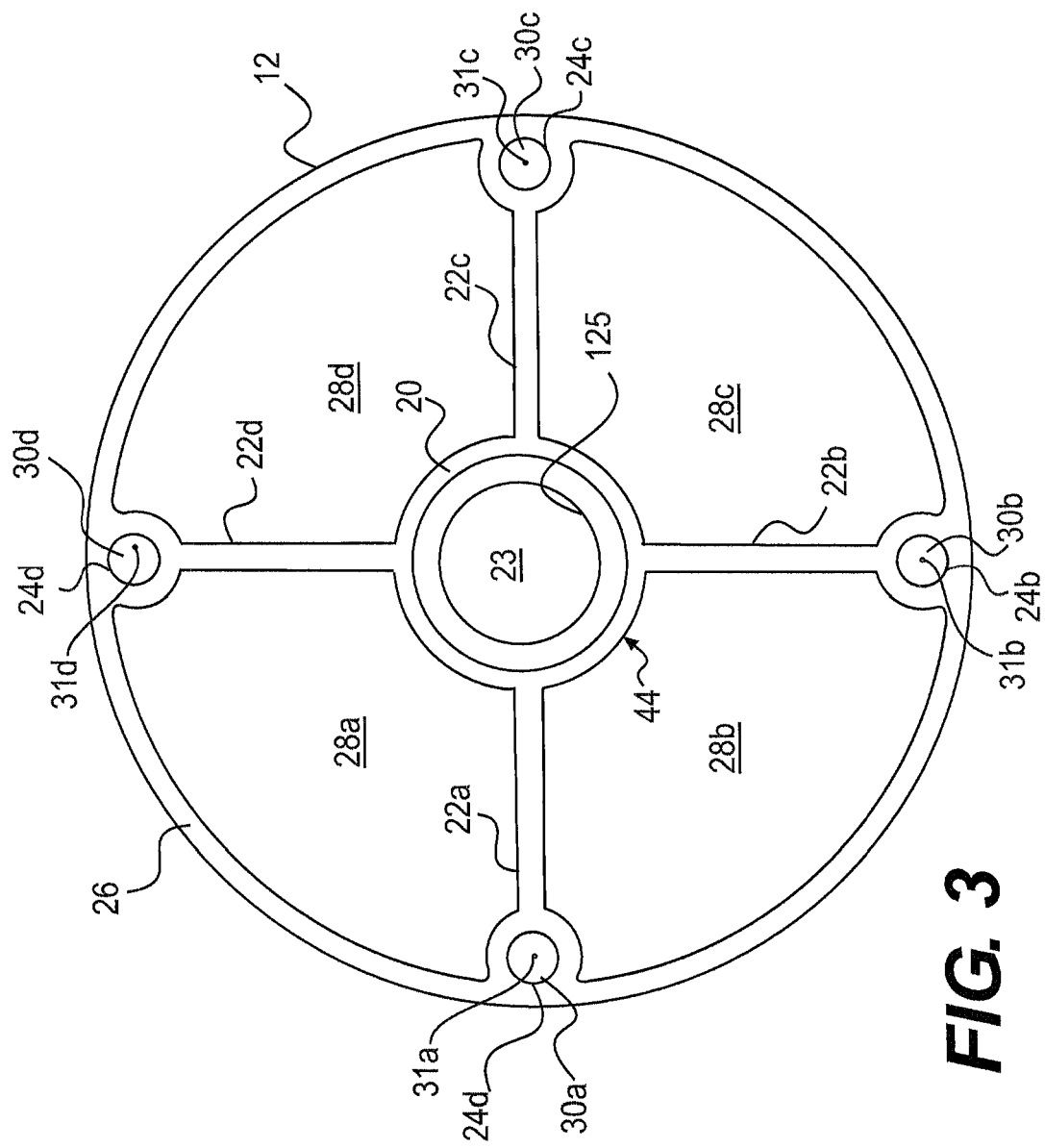
FIG. 3 illustrates a plan view of one embodiment of an articulation link, in accordance with the disclosed technology.

As shown in FIGS. 2 and 3, elongate body 20 can also include a distal end 40, a proximal end 42, and an outer surface 44. As explained below, distal end 40 of articulation link 14 may be configured to moveably engage proximal end 42 of a proximally-located adjacent articulation link 12. This relative movement can permit selective bending of articulating portion 9.

As shown in FIGS. 2 and 3, each articulation link 12-18 can also include two or more arms 22a, 22b, 22c and 22d that may extend radially outwards from elongate body 20. Specifically, arm 22 may extend outwards from an outer surface 44 of elongate body 20. In the embodiments shown herein, each articulation link 12-18 has four radially extending arms 22a-22d equally spaced about elongate body 20. However, it will be appreciated that a greater or lesser number of arms 22a-22d, and unequal arm spacing, could be used. For example, some articulation links 12-18 may include two arms 22 while others may have three or more arms 22.

As shown in FIG. 3, each of the outer ends of the arms 22a-22d can include, respectively, a second lumen 24a-24d. Second lumen 24 can also be located anywhere along arm 22. Further, second lumens 24a-24d can be aligned generally parallel to longitudinal axis 19 of elongate body 20. Moreover, each second lumen 24a-24d of articulation link 12 may be in longitudinal alignment with corresponding second lumens 24a-24d of other articulation links 14-18. Because second lumen 24 can be configured to receive a control member 30, aligning second lumens 24a-24d along common longitudinal axes allows for placement of control members 30a-30d through the commonly aligned second lumens 24a-24d. The second lumens 24a-24d may be positioned away from the pivoting axis.

As shown in FIG. 2, a single control member 30 can be positioned within a plurality of corresponding second lumens 24a-24d located on a plurality of articulation links 12-18. Each set of corresponding second lumens 24a-24d, stacked longitudinally and aligned on a common longitudinal axis, can receive a common control member 30a-30d. For example, control member 30a can pass through a plurality of second lumens 24a, wherein each second lumen 24a is generally aligned along a common longitudinal axis 31a. Similarly, control member 30b can pass through corresponding second lumens 24b on at least articulation links 12-18, wherein each second lumen 24b is generally aligned along a common longitudinal axis 31b.

Longitudinal axes 31a and 31b can be parallel and laterally displaced from each other or from longitudinal axis 19. Thus, when articulation joint 10 is in a generally straight configuration, control members 30a-d can be generally parallel to each other. As such, control members 30a-d can have longitudinal axes 31a-d that are generally parallel to and laterally displaced from each other.

In operation, a single control member 30 can pass freely through one or more articulation links 12-18 to selectively move articulation joint 10. One or more control members 30 may extend through shaft 4 and terminate at a distal region of shaft 4, for example, at a most distal link. In some embodiments, a handle, lever, dial, or control knob can be moved to selectively tension one or more control members 30 to steer distal end 8 of shaft 4 in a desired direction.

Control member 30 can include a wire, a cable, a ribbon, a rod, or any suitable elongate member. Control member 30 can include a distal end, a stop, a loop, or other mechanism that secures it to a distal-most or a proximal-most articulation link so that it does not pull through articulation links 12-18. It is also contemplated that at least part of control member 30 can include an outer sheath and an inner core wire. In some embodiments, the outer sheath can be sized to frictionally engage second lumen 24 of articulation link 12, a distal-most articulation link, or a proximal-most articulation link.

In the embodiment shown in FIGS. 2 and 3, a support member 26 extends generally around the outer ends of the arms 22a-22d. Support member 26 may be configured to provide rigidity to one or more arms 22, such as, for example, torsional rigidity. Also, support member 26 may extend between two or more arms 22 and may be any suitable shape, such as, for example, a radial hoop. In some embodiments, support member 26 may include a straight member or may extend generally from a mid-point of one or more arms 22.

As shown in FIG. 3, articulation link 12 can include a number of spaces 28a-28d in the areas between arms 22a-22d. A tube, shaft, wire, or other component of a medical instrument could be routed through spaces 28a-28d. It is also contemplated that a working channel or other elongate structure could be routed through the center of first lumen 23 within bending member 125. For example, one or more flexible endoscopic instruments could be passed through lumen 23 and/or spaces 28a-28d.

To permit movement of articulation joint 10, articulation links 12-18 may include one or more contact surfaces configured to permit relative movement between articulation links 12-18. A contact surface may also be configured to reduce or prevent adjacent articulation links 12-18 from rotating about longitudinal axis 19 with respect to each other while allowing deflection from longitudinal axis 19. For example, FIG. 4 shows a bent articulation joint 10 deviating from longitudinal axis 19.

In one embodiment, a contact surface can include a concave or a convex surface. As shown in FIG. 4, articulation link 14 can include one or more convex surfaces 32 located at proximal end 42 of elongate body 20 that fit within corresponding one or more concave surfaces 34 located at distal end 43 of articulation link 12. Articulation link 14 can also include a second contact surface 38 located at the distal end 40 of elongate body 20.

Figure 4:
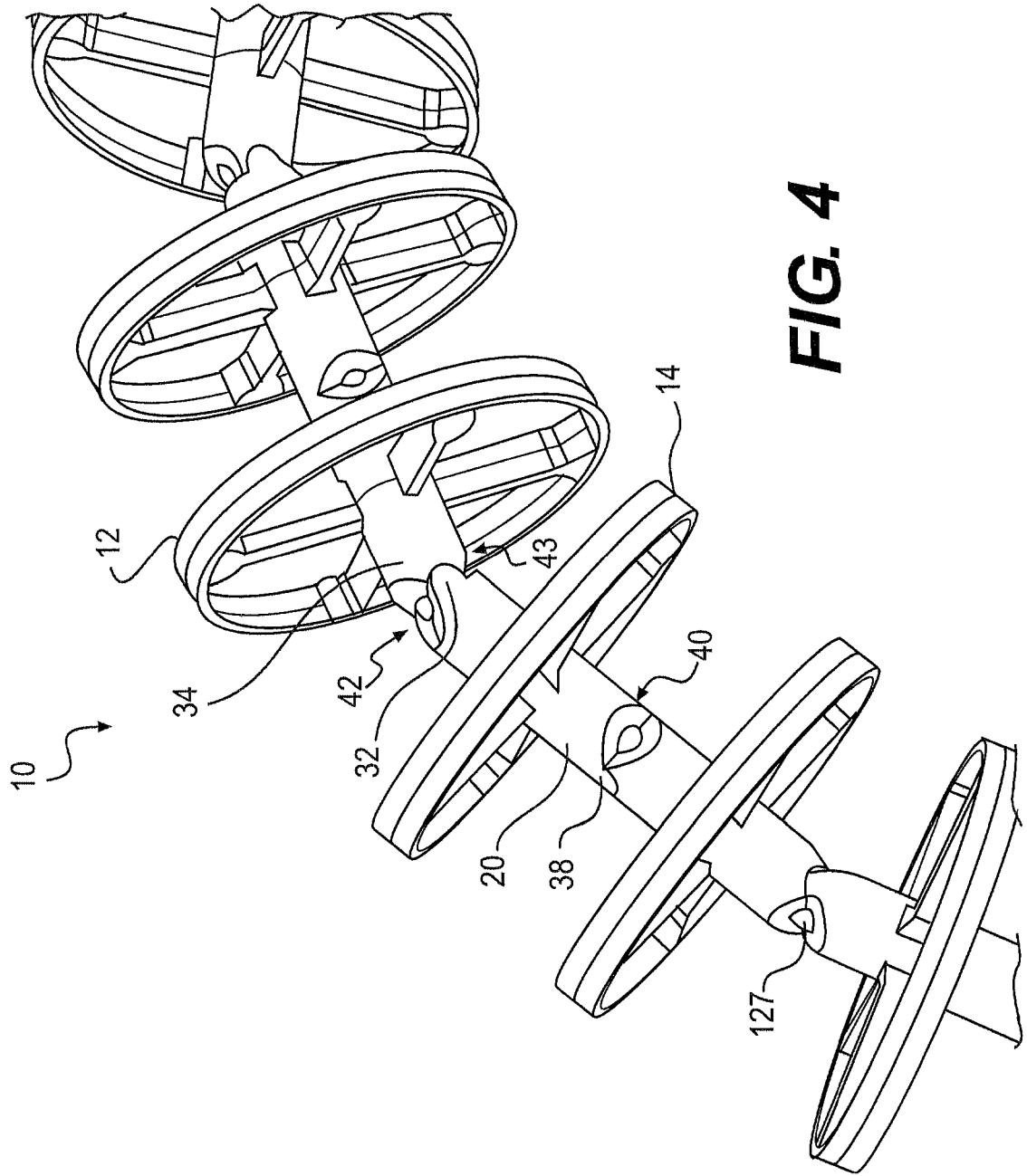
FIG. 4 illustrates a bent articulation joint, according to an exemplary embodiment of the invention.

In the embodiment shown in FIG. 4, contact surface 32 and contact surface 38 at each end of elongate body 20 are offset and rotated about the longitudinal axis by 90° with respect to each other. Such an offset of contact surfaces permits adjacent articulation links to pivot in different directions relative to each other, wherein each direction is offset by 90° relative to the other. This allows, for example, left-right and up-down movement of articulation joint 10. Other embodiments can include no offset or a different angle of offset.

In other embodiments, articulation link 12 can include one or more pivoting surfaces (not shown). Pivoting surfaces can include a joint or a hinge configured to allow pivoting between adjacent articulation links. Other types of couplings between articulation links 12-18 are also possible. For example, contact surfaces can include a ball and socket type coupling, whereby the "ball" contact surface of an articulation link couples with corresponding "socket" contact surface on an adjacent articulation link.

Figure 5:
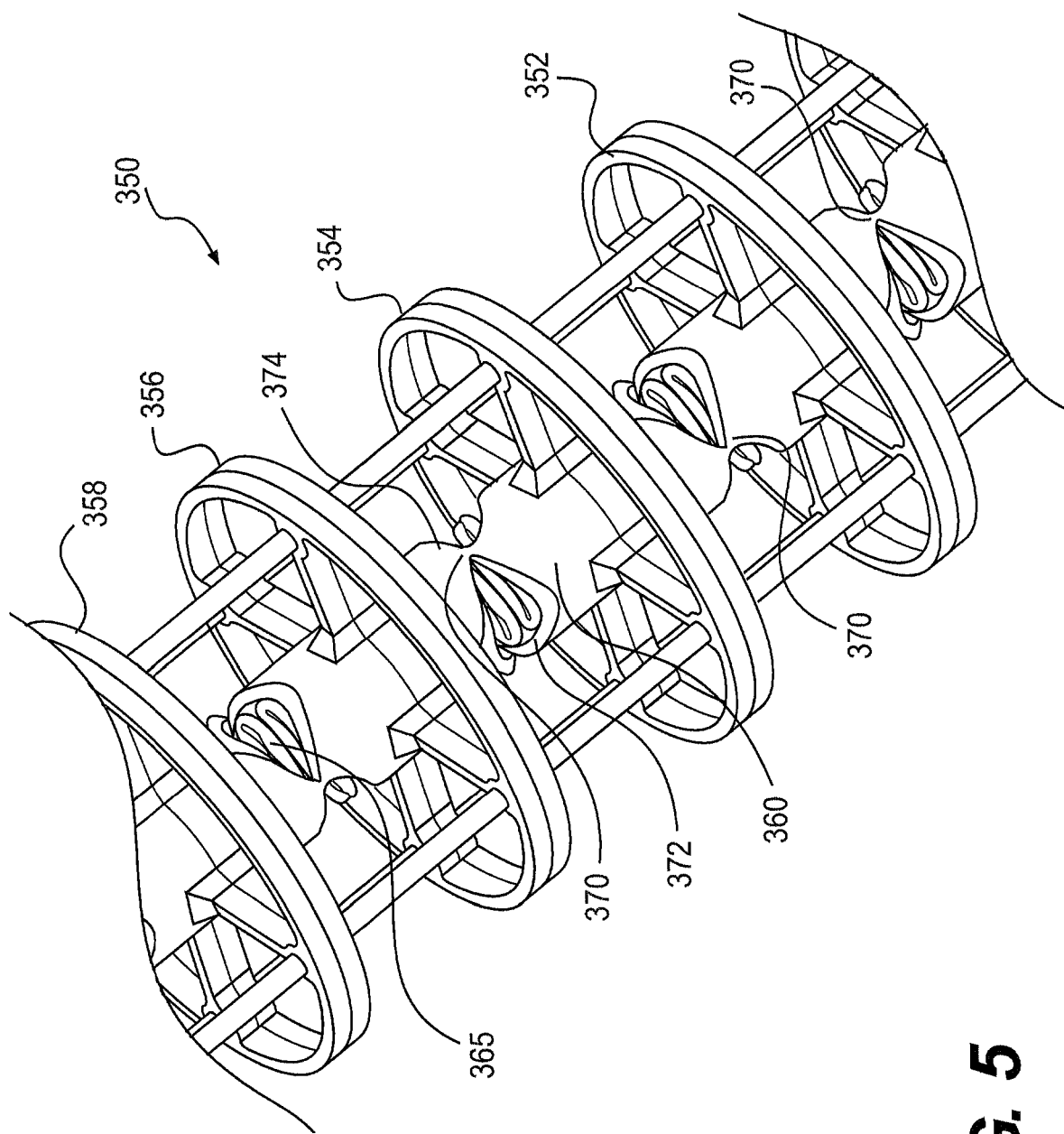
FIG. 5 illustrates another embodiment of an articulation joint, according to an exemplary embodiment of the invention.

In contrast to the embodiments shown above, the adjacent articulation links shown in FIG. 5 are joined by a flexible section 370. In particular, an articulation joint 350 has a number of articulation links 352-358. As shown, each articulation link 352-358 includes an elongate body 360, a spring 365 extending therethrough, and a number of radial arms with lumens for receiving a control member, as previously described. Flexible section 370 can include a living hinge formed using a plastic material. In some embodiments, a V-shaped notch may provide sufficient flexibility to operate as a hinge-like device. For example cutouts 372 and 374 located on either side of flexible section 370 can define the extent of bending that can occur between adjacent articulation links. Adjacent flexible sections 370 can also be alternating in their alignment and offset by 90°, as shown.

Figure 6:
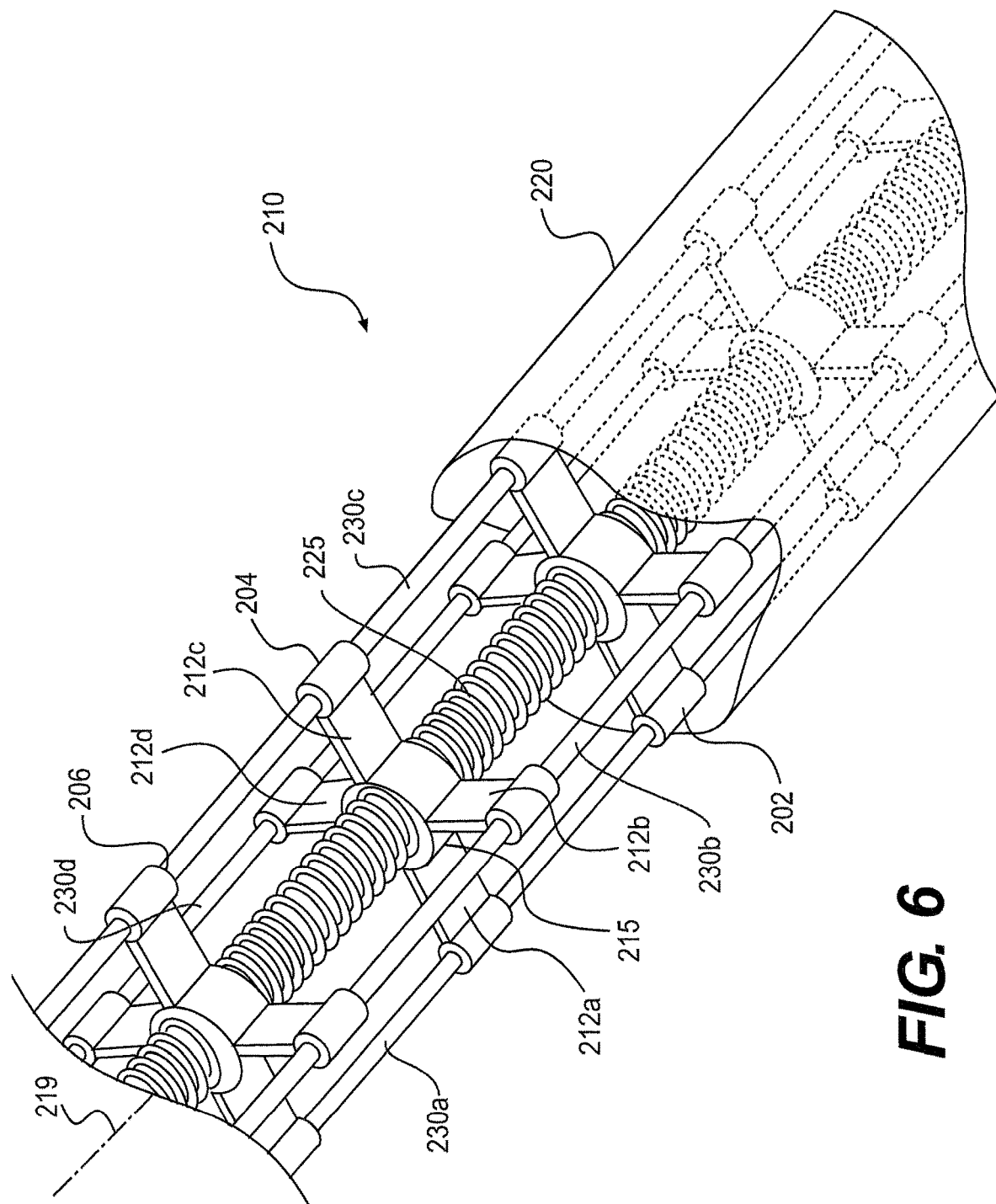
FIG. 6 illustrates another articulation joint, according to an exemplary embodiment of the invention.

FIG. 6 illustrates another alternative embodiment of an articulation joint 210. Specifically, articulation joint 210 includes a number of articulation links 202, 204, and 206 that are physically separated along a longitudinal axis 219.

Separating articulation links 202-206 can permit greater flexibility of articulation joint 210, reduce wear to articulation links 202-206, or simplify manufacture of articulation joint 210.

Figure 7:
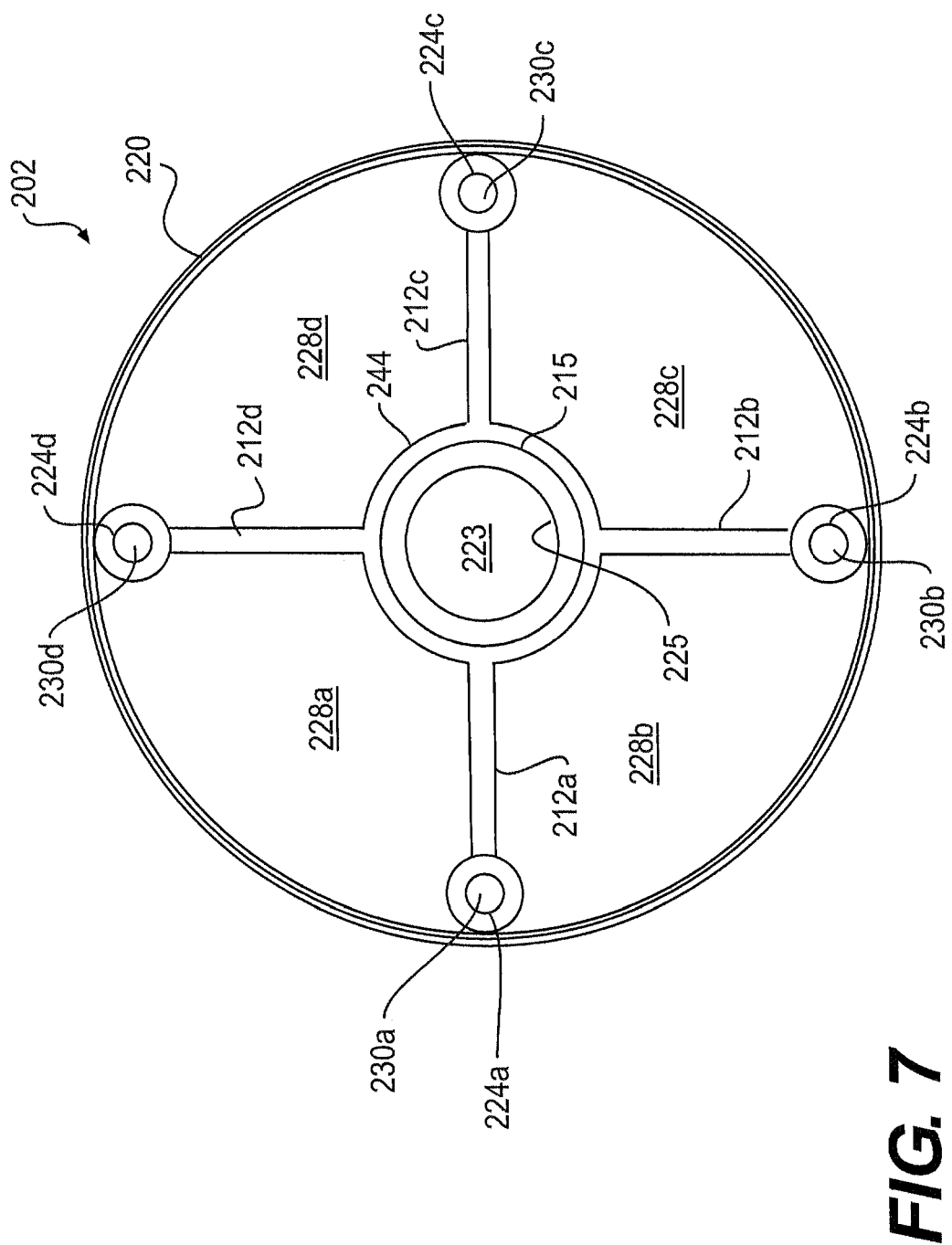
FIG. 7 illustrates a plan view of a link of an articulation joint having no support member, according to an exemplary embodiment of the invention.

FIGS. 6 and 7 show an elongate body 215 having a first lumen 223 extending therethrough and surrounding bending member 225. Articulation link 202 can also include various numbers of arms 212. As shown in FIG. 7, articulation link 202 includes four arms 212a-212d extending radially outward from an outer surface 244 of elongate body 215. The outer ends of arms 212a-212d include second lumens 224a-224d configured to receive control members 230a-230d. As previously explained, although FIGS. 6 and 7 show four radially extending arms 212a-212d, a lesser or greater number of arms could be included depending, for example, upon the number of control members 230a-d.

In contrast to the embodiments shown above, articulation links 202-206 do not include any support structure connecting two or more arms 212a-212d. Cover 220 can extend about one or more articulation links 202-206. As described above, the spaces between arms 212a-212d and cover 220 may define a number of spaces 228a-228d. Cover 220 may aid in transmitting torque along the length of articulation joint 210 or form a protective outer surface of articulation joint 210. Cover 220 may include a braid, a wire, a mesh, or other material that may aid in transmitting torque along articulation joint 210.

Figure 8:
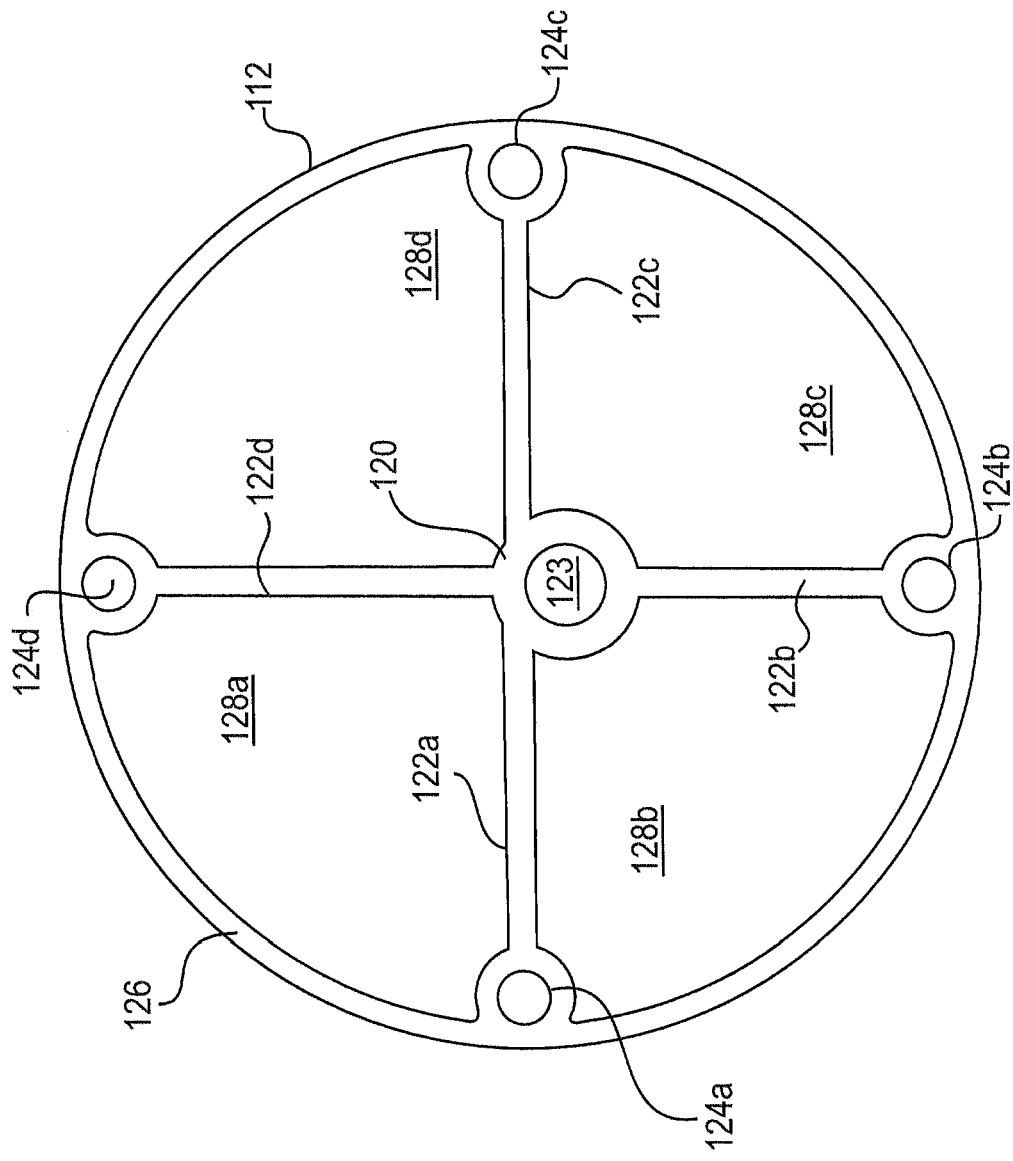
FIG. 8 illustrates a plan view of a link of an articulation joint having an eccentric center channel, according to an exemplary embodiment of the invention.

FIG. 8 is a cross-sectional view of a single articulation link 112, according to another exemplary embodiment. As shown, articulation link 112 can include an elongate body 120 having a first lumen 123 and a number of radially extending arms 122a-122d, wherein each arm can include a second lumen 124a-124d. As explained above, control members (not shown) can be passed through one or more second lumens 124a-124d and support member 126 may link the outer ends of the arms 122a-122d.

In the embodiment shown, elongate body 120 and lumen 123 are asymmetrically located from the center of articulation link 112. That is, elongate body and lumen 123 are centered on a longitudinal axis that is offset with respect to the central longitudinal axis of articulation link 112. This can permit preferential bending in a single direction of an articulation joint formed from such articulation links 112. In the embodiment shown in FIG. 8, articulation link 112 can bend more easily in the direction of arm 122d due to the greater length of the arm 122d with respect to the remaining arms 122a-122c.

The embodiments described herein are exemplary only, and it will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only, with a true scope of the invention being indicated by the following claims.

We claim:

1. An articulation assembly comprising:
   an articulation link including:
   a body defining a first lumen; and
   a plurality of arms extending radially outward from the body, wherein each arm of the plurality of arms includes:
   a first end coupled to an outer surface of the body, and
   a second end defining a second lumen; and
   a bendable member positioned within the first lumen, wherein the bendable member defines a third lumen configured to receive a medical device.

2. The articulation assembly of claim 1, wherein the second lumen has a longitudinal axis that is transverse to a longitudinal axis of a respective arm of the plurality of arms.

3. The articulation assembly of claim 1, wherein the articulation link includes a contact surface configured to engage an adjacent articulation link to permit relative movement between the articulation link and the adjacent articulation link, wherein the contact surface includes at least one of a camming surface, a pivoting surface, a concave surface, or a convex surface.

4. The articulation assembly of claim 1, wherein a central longitudinal axis of the first lumen is offset from a central longitudinal axis of the articulation link.

5. The articulation assembly of claim 1, wherein the plurality of arms are distributed symmetrically about the outer surface of the body.

6. The articulation assembly of claim 1, wherein the articulation link is one of a plurality of articulation links having a common longitudinal axis, wherein each articulation link of the plurality of articulation links includes:
   the body defining a first lumen; and
   the plurality of arms extending radially outward from the body, wherein each arm of the plurality of arms includes:
   the first end coupled to an outer surface of the body, and
   the second end defining a second lumen.

7. The articulation assembly of claim 6, wherein the bendable member is exposed at a gap between opposing surfaces of adjacent articulation links of the plurality of articulation links.

8. The articulation assembly of claim 1, wherein a proximal end of the body includes a proximal contact surface configured to engage a proximally-located adjacent articulation link, wherein a distal end of the body includes a distal contact surface configured to engage a distally-located adjacent articulation link, and wherein the proximal contact surface is offset 90° relative to the distal contact surface.

9. The articulation assembly of claim 1, wherein the plurality of arms extend transverse to a longitudinal axis of the body.

10. The articulation assembly of claim 1, further comprising a plurality of control members, wherein each of the plurality of control members is positioned within the second lumen of a respective arm of the plurality of arms.

11. The articulation assembly of claim 1, wherein two arms of the plurality of arms and a cover positioned around the plurality of arms define a space configured to receive a second medical device.

12. An articulation assembly comprising:
   an articulation link including:
   a body defining a first lumen; and
   a plurality of arms, wherein each arm of the plurality of arms includes:
   a first end portion coupled to an outer surface of the body;
   a middle portion having extending radially outward from the body; and
   a second end portion, wherein a width of the second end portion, in a direction perpendicular to a longitudinal axis of the arm, is greater than a width of the middle portion, and wherein the second end portion defines a second lumen; and
   a control member positioned within the second lumen of at least one arm of the plurality of arms.

13. The articulation assembly of claim 12, further comprising a bendable member positioned within the first lumen, wherein the bendable member defines a lumen configured to receive a medical device.

14. The articulation assembly of claim 12, wherein the articulation link includes a contact surface configured to engage an adjacent articulation link to permit relative movement between the articulation link and the adjacent articulation link, wherein the contact surface includes at least one of a pivoting surface, a concave surface, or a convex surface.

15. The articulation assembly of claim 12, wherein a central longitudinal axis of the first lumen is offset from a central longitudinal axis of the articulation link.

16. The articulation assembly of claim 12, wherein the articulation link is one of a plurality of articulation links, and wherein the control member is exposed at a gap between opposing surfaces of adjacent articulation links of the plurality of articulation links, and wherein each articulation link of the plurality of articulation links includes:
    the plurality of arms, wherein each arm of the plurality of arms includes:
        the first end portion coupled to the outer surface of the body;
        the middle portion having extending radially outward from the body; and
        the second end portion, wherein the width of the second end portion, in the direction perpendicular to the longitudinal axis of the arm, is greater than the width of the middle portion, and wherein the second end portion defines the second lumen.

17. An articulation assembly comprising:
    a plurality of articulation links, wherein each articulation link of the plurality of articulation links includes:
        a body defining a first lumen; and
        a plurality of arms extending radially outward from the body, wherein each arm of the plurality of arms includes:
            a first end coupled to an outer surface of the body, and
            a second end defining a second lumen; and
    a control member positioned within the second lumen of at least one arm of the plurality of arms of each articulation link of the plurality of articulation links, wherein the control member is exposed at a gap between opposing surfaces of adjacent articulation links of the plurality of articulation links when the second lumens of the adjacent articulation links have parallel central longitudinal axes.

18. The articulation assembly of claim 17, further comprising a bendable member positioned within the first lumen of each articulation link of the plurality of articulation links, wherein the bendable member defines a lumen configured to receive a medical device.

19. The articulation assembly of claim 17, wherein the control member is exposed at the gap.

* * * * *